United States Patent [19]

Campbell et al.

[11] 4,105,857
[45] Aug. 8, 1978

[54] PROCESS FOR PREPARING PHENYL TRICHLORO-ETHANES

[75] Inventors: John R. Campbell; Howard J. Klopfer, both of Clifton Park, N.Y.

[73] Assignee: General Electric Company, Schenectady, N.Y.

[21] Appl. No.: 784,345

[22] Filed: Apr. 4, 1977

[51] Int. Cl.² .............................................. C07C 37/00
[52] U.S. Cl. ................................ 568/726; 260/613 R
[58] Field of Search ........................ 260/613 R, 619 A

[56] References Cited

U.S. PATENT DOCUMENTS

| | | | |
|---|---|---|---|
| 2,435,014 | 1/1948 | Niederl | 260/619 A |
| 2,572,141 | 10/1951 | Harris | 260/613 R |
| 2,698,866 | 1/1955 | Churchill | 260/619 A |
| 2,766,293 | 10/1956 | Miville | 260/619 A |

*Primary Examiner*—Bernard Helfin
*Attorney, Agent, or Firm*—Joseph T. Cohen; Charles T. Watts; Marvin Snyder

[57] ABSTRACT

Diphenyl trichloro-ethanes can be prepared by effecting reaction between a phenol or anisole (methoxybenzene) with chloral in a solvent medium comprising sulfuric acid and a liquid aliphatic chlorohydrocarbon containing from 1 to 2 carbon atoms.

2 Claims, No Drawings

PROCESS FOR PREPARING PHENYL TRICHLORO-ETHANES

This invention relates to a process for making trichloro diphenyl ethanes. More particularly, the invention is concerned with the process for making a trichloro-ethane of the formula

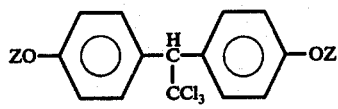   I which comprises reacting under condensation conditions an aryl compound of the formula

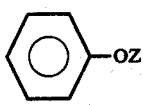   II which chloral in a solvent medium comprising sulfuric acid and a liquid aliphatic chlorohydrocarbon compound containing from 1 to 2 carbon atoms, where Z is a member selected from the class consisting of hydrogen and the methyl radical.

Diphenyl trichloro-ethanes such as 1,1,1-trichloro-2,2-bis(4-hydroxyphenyl)ethane have in the past been prepared by the condensation of phenol and chloral in a solvent medium comprising sulfuric acid and acetic acid. [See E. TerMeer, Ber., 7, 1201 (1874); E. Von Auwers, Ber., 36, 1878 (1889).] While the crude product obtained by this method is in an acceptable yield, it is generally highly colored and contaminated with substantial qualtities of by-products, notably 1,1,1-trichloro-2-(4-hydroxyphenyl)-2-(2-hydroxyphenyl)ethane (hereinafter identified as "o,p-isomer"). In addition to the above disadvantages, the use of acetic acid increases the cost of the process. Moreover, the rate at which the reaction occurs is fairly slow, and because of the high heat of reaction, it is necessary to introduce highly sophisticated cooling means, which again adds to the cost of the process.

We have now discovered that the above reaction between the aryl compound and the chloral can readily take place in sulfuric acid if the acetic acid is replaced by a liquid aliphatic chlorohydrocarbon containing from 1 to 2 carbon atoms, and that by using such a chlorohydrocarbon, numerous advantages are derived.

In the first place, these chlorohydrocarbons represent a much lower cost investment than does the acetic acid. In addition, the lower boiling points of these chlorohydrocarbons offer a much better environment for recycling, and it has been found that the rate of reaction between the aryl compound and the chloral proceeds at a much faster rate in the presence of the chlorinated hydrocarbon. Also, the chlorohydrocarbon exerts a moderating influence on the temperature at which the reaction is carried out, so it is only necessary to cary the reaction at a maximum of the reflux temperature of the mass, and thus cooling means are held to a minimum. Finally, we have discovered that the impurities obtained in the reaction using the chlorohydrocarbon are often much less than when using the acetic acid, in particular, such impurities as the carbinols

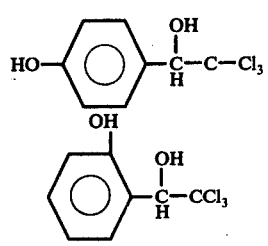

which are respectively identified as the "p-carbinol" and the "o-carbinol." By using the chlorohydrocarbon, the color is usually better at any stage of the process, and the rate of reaction, that is, rate of generation of the diphenyl trichloroethane derivative, is at least 5 to 6 times that when using the acetic acid.

Among the chlorohydrocarbons which may be employed are, for instance, methylene chloride, chloroform, carbon tetrachloride, 1,2-dichloro-ethane, tetrachloroethylene, etc. Mixtures thereof are not precluded. The important thing is that the chlorohydrocarbon used be liquid at room temperatures (about 25°-30° C.) and that it be a solvent for the reactants.

The sulfuric acid employed is aqueous sulfuric acid of a concentration of at least 90% $H_2SO_4$. Below 90% $H_2SO_4$, the reaction rate becomes sluggish. Percent $H_2SO_4$ as high as 100% can be used, however, advantageously we employ from 90 to 98% $H_2SO_4$ to reduce the chances for sulfonation of the aromatic rings.

The temperature at which reaction may be carried out may be varied widely, recognizing that at lower temperatures the rate is less rapid than at elevated temperatures. Generally, temperatures ranging about 10° to about 50° C. are advantageously employed and for the most part the reflux temperature of the mass is usually sufficient for carrying out the reaction. The use of superatmospheric pressure is not precluded, and when such superpressures are used, temperatures in excess of 50° C., for example, 75° to 100° C. or higher, may be employed up to the decomposition point of either the reactant or the reaction product.

The mixture of the sulfuric acid and chlorohydrocarbon in proportion to the other reactants can be varied widely and is not critical. Generally, on a weight basis, we can employ from about 0.75 to 10 or more parts of the mixture of the sulfuric acid and chlorohydrocarbon per part of the aryl compound. The weight ratio of the chlorohydrocarbon to the sulfuric acid may also be varied widely, and again is not critical. Generally, the amount of the two members of the solvent medium should range, on a weight basis, of from 0.5 to 10 parts of the chlorohydrocarbon per part of sulfuric acid. If more of the chlorohydrocarbon is employed, it will be found that the rate of reaction may drop off, while if more of the sulfuric acid is used, it will be found that the reaction mixture increases in viscosity and will cause some stirring difficulties.

Molar concentrations of the aryl compound and the chloral can be varied widely as long as there are present at least 2 mols of the aryl compound per mol of the chloral. Advantageously, one can employ from about 2.0 to about 5 mols of the aryl compound per mol of the chloral in order to ensure completion of the reaction to form the desired diphenyl trichloro-ethane.

In order that those skilled in the art may better understand how the present invention may be practiced, the following examples are given by way of illustration and not by way of limitation. All parts are by weight unless otherwise designated. In all the examples, stirring was maintained throughout the reaction while a nitrogen blanket was present over the reaction medium. Because the reaction is exothermic, cooling was resorted to in order to maintain the designated temperatures.

Analyses of the reaction products in some of the following examples to determine the presence of the desired materials and other ingredients, was carried out by silylating samples of the isolated reaction product with bis(trimethylsilyl) acetamide in the manner described by Klebe et al in J.A.C.S. 88, 3390 (1966). This involved adding a previously silylated weighed sample of bisphenol-A to serve as an internal standard. The silylated mixture was then analyzed by vapor phase chromatography using a 6' × φ inches Se-30 column with a temperature program of 150° to 300° C. at 10° C per minute. VPC (vapor phase chromatographic) retention times for 2,2,2-trichloro-1-(4-hydroxyphenyl)ethanol (formula III), 2,2,2-trichloro-1-(2-hydroxyphenyl) ethanol (formula IV), the o,p-isomer having the formula

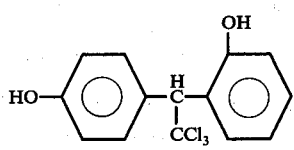

V and the p,p-isomer (which is the more desirable isomer for making polycarbonate resins by phosgenation) having the formula

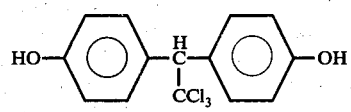

VI are 7.0, 8.2, 12.0, and 13.0 minutes, respectively.

Example 1 was carried out using a mixture of sulfuric acid and acetic acid (as taught in the prior art) as the medium in which the reaction is conducted between the aryl compound, in this case phenol, and chloral, This example serves as a standard for comparison with some of the succeeding examples wherein the acetic acid is replaced by methylene chloride or other chlorinated aliphatic hydrocarbon.

EXAMPLE 1

A reaction vessel equipped with stirrer, thermometer, nitrogen inlet and addition funnel was charged with 87.1 grams 96% sulfuric acid, 86.7 grams phenol (0.922 mol) and 49.3 grams acetic acid. The reaction mixture was cooled to maintain the temperature between 16°-18° C. Thereafter, 47.7 grams (0.324 mol) chloral was added dropwise, again with cooling (since the reaction is mildly exothermic) to maintain the appropriate temperature (see Table 2 for effect of varying temperature) over a 45 minute period to the stirred reaction mixture. The reaction mixture was analyzed by silylation as described above, and the results of the tests are shown in Table 1. The crude product isolated by water quench of this reaction mixture was highly colored, ranging from pinkish to almost purple in color.

TABLE 1

| Time | % Yield Based on Chloral | | | |
|---|---|---|---|---|
| (hours) | o-carbinol | p-carbinol | o,p-isomer | p,p-isomer |
| 0.367 | 1.8 | 7.9 | 0 | 4.6 |
| 1.41 | 3.7 | 21.3 | 0.8 | 25.1 |
| 2.03 | 4.1 | 21.2 | 1.8 | 37.7 |
| 3.25 | 4.2 | 15.2 | 2.8 | 60.0 |
| 4.17 | 3.9 | 9.9 | 3.7 | 72.2 |
| 5.95 | 3.5 | 4.5 | 4.5 | 83.1 |
| 22.83 | 0 | 1.5 | 5.7 | 88.4 |

The following Table 2 shows the results of carrying out the above-identified reaction in Example 1 using the sulfuric acid — acetic acid solvent medium at different times and temperatures.

TABLE 2

| Temperature | Time | % o,p-isomer | % p,p-isomer |
|---|---|---|---|
| 4° C. | 72 hrs. | 5.0 | 88.5 |
| 28° C. | 1.25 hrs. | 2.9 | 57.1 |
| 28° C. | 2.25 hrs. | 4.6 | 78.2 |
| 28° C. | 7 hrs. | 7.7 | 90.4 |

The following Example 2 shows the results of carrying out the reaction between the phenol and the chloral in a solvent medium comprising the sulfuric acid and methylene chloride (in place of the acetic acid).

EXAMPLE 2

Example 1 was repeated employing the same conditions as in Example 1 and the same reactants and concentration of reactants with the exception that 87.6 grams of 96% sulfuric acid and 62.5 grams of methylene chloride were substituted for the sulfuric acid and acetic acid described in Example 1. The following Table 3 shows the results of carrying out this reaction at a temperature of about 16° C. for various periods of time. The solid product was slightly off-white in color.

TABLE 3

| Time | % Yield Based on Chloral | | | |
|---|---|---|---|---|
| (hours) | o-carbinol | p-carbinol | o,p-isomer | p,p-isomer |
| 0.375 | 2.4 | 1.7 | 4.2 | 51.5 |
| 0.750 | 5.6 | — | 5.6 | 83.1 |
| 1.0 | 3.8 | 2.4 | 6.2 | 84.7 |
| 1.25 | — | — | — | 88.9 |
| 1.50 | 3.2 | 1.3 | 8.6 | 89.6 |
| 2.16 | 0.5 | 0.6 | 9.4 | 89.6 |

EXAMPLE 3

When the reaction in Example 1 was repeated with the exception that no acetic acid was used, it was found that after about ¾ hour, 48.2% of the p,p-isomer based on the chloral used was obtained. However, after heating for a total of 2¾ hours, the yield of the p,p-isomer had decreased to 6.4%.

EXAMPLE 4

Employing the same conditions as recited in Example 1, 87.1 grams 96% aqueous sulfuric acid, 99.6 grams (0.922 mol) anisole, 47.7 grams (0.324 mol) chloral were interacted at a temperature of from 16° to 22° C. for about 18 hours with stirring. Thereafter, the reaction mixture was allowed to stand for about 72 hours at room temperature (about 25°-30° C.) The reaction mixture was diluted with about 150 ml water, an amount of 150 ml methylene chloride was added to extract the organic phase, the methylene chloride solution washed with water, the methylene chloride evaporated, and the residue diluted with 250 ml methanol. The methanol solution was then cooled to 0° C. to cause crystallization of the desired product, which when filtered was found by vapor phase chromatography to be an isomeric mixture of methoxychloro derivatives having the general formula

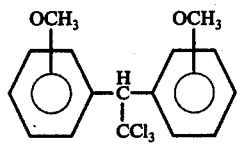   VII (where the methoxy groups are in the ortho or para positions) in good yield of which 90% was the para derivative of the formula

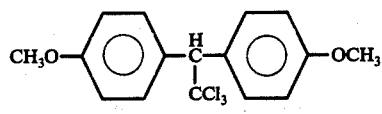   VIII and 10% was the o,p-derivative of formula

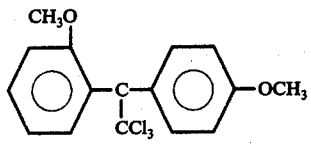   IX

EXAMPLE 5

In this example, the procedure of Example 1 was repeated with the exception that the same volume of acetic acid was replaced on a one-to-one volume basis by chloroform, 1,2-dichloro-ethane, or carbon tetrachloride for the purpose of illustrating the use of other chlorinated aliphatic hydrocarbons in place of the acetic acid in preparing the phenyl trichloro-ethanes of the instant invention. Again the same temperature was maintained as in Example 1, but this time for 3 hours. In each instance, good yields of the desired dihydroxy diphenyl trichloro-ethane of formula VI were obtained together with smaller amounts of the o,p-derivative of formula V. The following table shows the conditions under which each of the three chlorinated aliphatic hydrocarbons were employed and the results obtained as far as the yield of the desired products and by-products based on the chloral employed.

TABLE 4

| Time (hours) | % Yield Based on Chloral | | | |
|---|---|---|---|---|
| | o-carbinol | p-carbinol | o,p-isomer | p,p-isomer |
| Chloroform (69 grams) | | | | |
| 2.95 | 0.5 | 0.3 | 8.4 | 85.0 |
| 19.75 | — | — | 4.1 | 89.7 |
| 1,2-dichloro-ethane (59 grams) | | | | |
| 0.75 | 3.0 | 3.4 | 5.2 | 63.0 |
| 1.3 | — | — | — | 76.0 |
| 5.25 | — | — | 6.4 | 83.2 |
| CCl₄ (74.7 grams) | | | | |
| 3 | — | — | 8.0 | 72 |

In the following example, the amount of the 96% aqueous sulfuric acid was reduced while the amount of methylene chloride employed was increased compared to that described in Example 2 in order to maintain a constant volume of liquid medium.

EXAMPLE 6

In this example, 86.7 grams phenol, 21.8 grams (about one-fourth of usual amount) 96% aqueous sulfuric acid, 47.7 grams chloral, and 109.4 grams (82.6 ml) methylene chloride were reacted at a temperature of between 16° to 20° C. for varying times similarly as in Example 2. The following Table 5 shows the results of the products and by-products obtained after carrying out this reaction. The desired product was slightly off-white in color.

TABLE 5

| Time (hours) | % Yield Based on Chloral | | | |
|---|---|---|---|---|
| | o-carbinol | p-carbinol | o,p-isomer | p,p-isomer |
| 2.0 | 5.0 | 14.2 | 1.8 | 24.1 |
| 3.5 | 5.7 | 13.5 | 2.1 | 33.1 |
| 7.25 | 7.5 | 12.9 | 3.5 | 57.9 |
| 72.0 | 8.2 | 6.4 | 5.2 | 79.6 |
| *6.75 | 11.2 | 8.0 | 4.4 | 76.9 |

*Reaction at 43° C.

It will of course be understood by those skilled in the art that other conditions of reactions and ratios of ingredients can be employed without departing from the scope of the invention. For instance, the ratio of the mixture of sulfuric acid and the chlorinated aliphatic hydrocarbon to the aryl compound can vary depending on the weight ratio between the sulfuric acid and the chlorinated hydrocarbon; persons skilled in the art will have no difficulty in ascertaining optimum conditions taking into account the effects of varying the ratio of the sulfuric acid to the chlorinated hydrocarbon based on the above-described examples. Also, it will be evident that other chlorinated hydrocarbons may be employed in place of those described in the preceding examples without departing from the intended invention.

The compositions of matter obtained in accordance with the practice of the present invention have many uses. For instance, the methoxy derivatives corresponding to formula VIII can be used as an insecticide, and is sold under the name of "Methoxychlor."

The dihydroxy diphenyl trichloro-ethane of formula VI can be used as a precursor intermediate for making the monomer composition having the formula

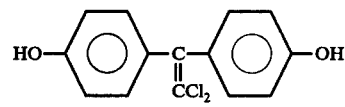

This latter dichloro-ethylene compound can be treated with a phosgenating agent such as phosgene, diphenyl carbonate, etc., to make polycarbonate resins which are useful in the preparation of flame-retardant and fire-resistant molded products such as housings for calculators, grills and dashboards for automobiles, etc.

What we claim as new and derive to secure by Letters Patent of the United States is:

1. The process for making a trichloro-ethane of the formula

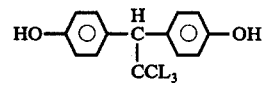

which comprises reacting under condensation conditions phenol and chloral in a solvent medium consisting essentially of methylene chloride and aqueous sulfuric acid of a concentration of from 90-98%.

2. The process as in claim 1 wherein the methylene chloride comprises, on a weight basis, from 0.5 to 10 parts of the latter per part of sulfuric acid.

* * * * *